(12) United States Patent
Jensen

(10) Patent No.: US 9,675,468 B1
(45) Date of Patent: Jun. 13, 2017

(54) HINGED SPINAL INSERT DEVICE

(71) Applicant: Wade K. Jensen, Dakota Dunes, SD (US)

(72) Inventor: Wade K. Jensen, Dakota Dunes, SD (US)

( * ) Notice: Subject to any disclaimer, the term of this patent is extended or adjusted under 35 U.S.C. 154(b) by 107 days.

(21) Appl. No.: 14/453,077

(22) Filed: Aug. 6, 2014

Related U.S. Application Data

(63) Continuation of application No. 13/838,045, filed on Mar. 15, 2013, now Pat. No. 8,828,085.

(51) Int. Cl.
*A61F 2/44* (2006.01)

(52) U.S. Cl.
CPC ...... *A61F 2/447* (2013.01); *A61F 2220/0016* (2013.01); *A61F 2220/0091* (2013.01); *A61F 2230/0086* (2013.01); *A61F 2250/0006* (2013.01)

(58) Field of Classification Search
CPC ............................... A61F 2/442; A61F 2/4425
USPC ...................... 606/246–249; 623/17.11–17.16
See application file for complete search history.

(56) References Cited

U.S. PATENT DOCUMENTS

| | | | |
|---|---|---|---|
| 8,025,697 B2* | 9/2011 | McClellan, III | A61F 2/447 623/17.11 |
| 2010/0137987 A1* | 6/2010 | Diao | A61B 17/8852 623/17.15 |
| 2011/0307066 A1* | 12/2011 | Lim | A61B 17/025 623/17.16 |
| 2012/0071977 A1* | 3/2012 | Oglaza | A61B 17/7065 623/17.11 |

* cited by examiner

*Primary Examiner* — Ellen C Hammond
*Assistant Examiner* — Christina Negrellirodrigue

(57) ABSTRACT

A spinal insert device adjusts inter-vertebral spacing and alignment of the spine relative to pelvic incidence, pelvic tilt and overall sagittal alignment. The device includes an upper arm having a substantially planar upper surface and a lower arm having a substantially planar lower surface. Each of the upper arm and the lower arm extends outwardly from a base section. A hinge couples the upper arm to the base section such that the upper arm is pivotable relative to the base section. An adjustment member is positioned between the upper arm and the lower arm. The adjustment member has a plurality of distinct lengths measured straight through a center of the adjustment member. The adjustment member is rotatable wherein an angle between the upper arm and the lower arm is selectively adjustable by rotation of the adjustment member.

32 Claims, 8 Drawing Sheets

FIG. 12

| Pelvic Incidence (degrees) | Total Lumbar Lordosis Applied (degrees) | Applied Between L1/L2 (degrees) | Applied Between L2/L3 (degrees) | Applied Between L3/L4 (degrees) | Applied Between L4/L5 (degrees) | Applied Between L5/S1 (degrees) |
|---|---|---|---|---|---|---|
| 35 | 45 | 5 | 5 | 5 | 15 | 15 |
| 40 | 50 | 5.5 | 5.5 | 5.5 | 17 | 17 |
| 45 | 55 | 6 | 6 | 6 | 18 | 18 |
| 50 | 60 | 7 | 7 | 7 | 20 | 20 |
| 55 | 65 | 7.5 | 7.5 | 7.5 | 22 | 22 |
| 60 | 70 | 8 | 8 | 8 | 23 | 23 |
| 65 | 75 | 8.5 | 8.5 | 8.5 | 25 | 25 |
| 70 | 80 | 9 | 9 | 9 | 27 | 27 |
| 75 | 85 | 9.5 | 9.5 | 9.5 | 28.3 | 28.3 |
| 80 | 90 | 10 | 10 | 10 | 30 | 30 |
| 85 | 95 | 10.5 | 10.5 | 10.5 | 32 | 32 |
| 90 | 100 | 11 | 11 | 11 | 33 | 33 |

HINGED SPINAL INSERT DEVICE

CROSS-REFERENCE TO RELATED APPLICATIONS

This application is a continuation of application Ser. No. 13/838,045 filed on Mar. 15, 2013.

BACKGROUND OF THE DISCLOSURE

Field of the Disclosure

The disclosure relates to spinal insert devices and more particularly pertains to a new spinal insert device for adjusting inter-vertebral spacing and alignment of the spine relative to pelvic incidence, pelvic tilt and overall sagittal alignment.

SUMMARY OF THE DISCLOSURE

An embodiment of the disclosure meets the needs presented above by generally comprising an upper arm having a substantially planar upper surface and a lower arm having a substantially planar lower surface. A base section is coupled to and extends between the upper arm and the lower arm defining a frame. Each of the upper arm and the lower arm extends outwardly from the base section. A hinge couples the upper arm to the base section such that the upper arm is pivotable relative to the base section. An adjustment member is positioned between the upper arm and the lower arm. The adjustment member has a plurality of distinct lengths measured straight through a center of the adjustment member. The adjustment member is rotatable wherein an angle between the upper arm and the lower arm is selectively adjustable by rotation of the adjustment member.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 12 is a graph of intervertebral spacing between adjacent vertebral endplates to achieve a desired cumulative spinal adjustment.

DESCRIPTION OF THE PREFERRED EMBODIMENT

Figure 1:
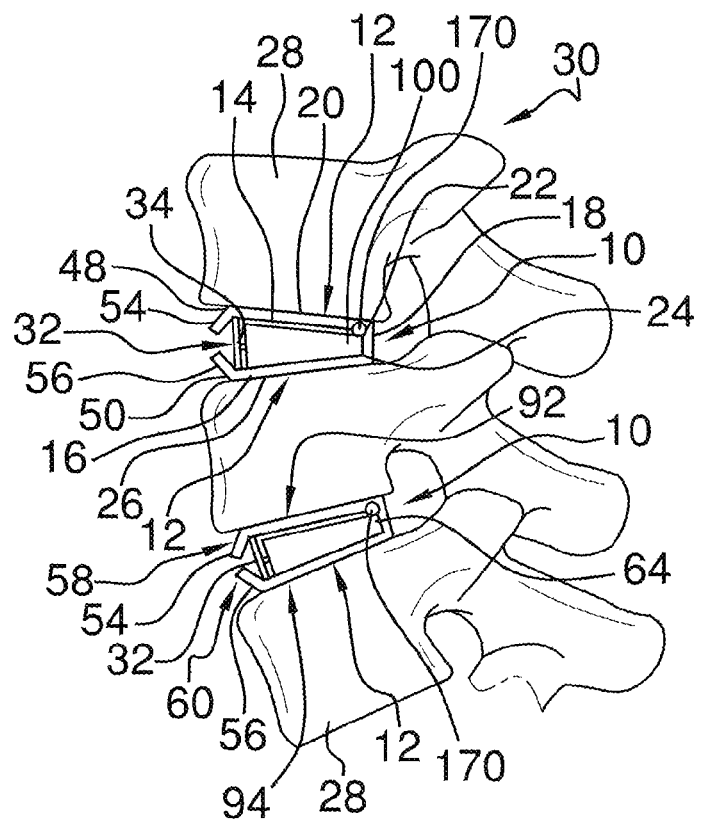
FIG. 1 is a side view of a spinal insert according to an embodiment of the disclosure.
Figure 2:
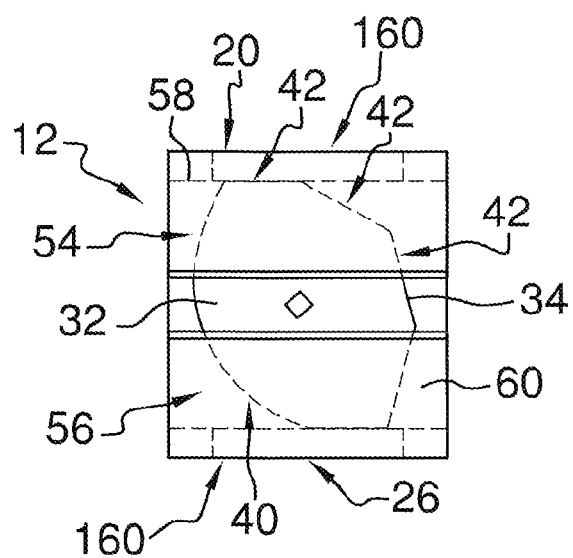
FIG. 2 is a front view of an embodiment of the disclosure.
Figure 3:
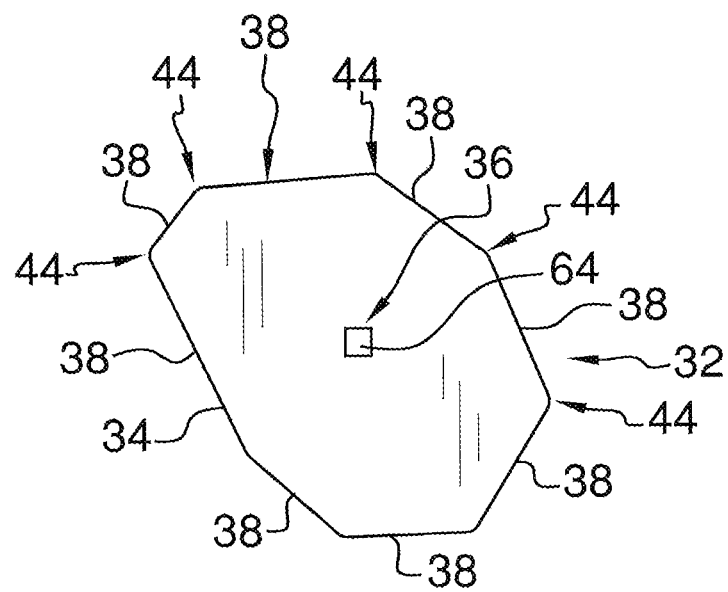
FIG. 3 is a back view of an adjustment member according to an embodiment of the disclosure.
Figure 4:
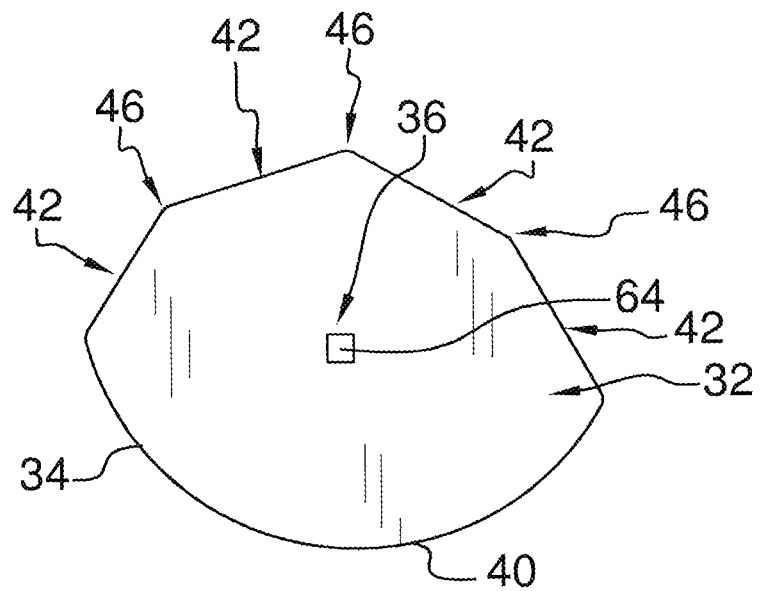
FIG. 4 is a back view of an adjustment member according to an embodiment of the disclosure.

With reference now to the drawings, and in particular to FIGS. 1 through 15 thereof, a new spinal insert device embodying the principles and concepts of an embodiment of the disclosure and generally designated by the reference numeral 10 will be described.

As best illustrated in FIGS. 1 through 15, an embodiment of the spinal insert device 10 generally comprises a frame 12 having a rigid upper arm 14, a rigid lower arm 16 and a base section 18 extending between proximal ends 22,24 of the upper arm 14 and the lower arm 16. Each of the upper arm 14 and the lower arm 16 extend outwardly from the base section 18. The upper arm 14 has a planar upper surface 20 and the lower arm 16 has a planar lower surface 26 each configured for and constructed of material suitable for abutting and fixation to vertebral bodies 28 of a spine 30. A hinge 170 couples the proximal end 22 of the upper arm 14 to the base section 18 wherein the upper arm 14 remains substantially planar but is pivotable relative to the base section 18.

An adjustment member 32 is positioned between the upper arm 14 and the lower arm 16. The adjustment member 32 may be disc-like and have an outer perimeter edge 34. The adjustment member 32 has a plurality of distinct lengths measured straight through a center 36 of the adjustment member 32 and straight across the adjustment member 32. Thus, the adjustment member 32 is rotatable wherein an angle between the upper arm 14 and the lower arm 16, and consequently an angle between the upper surface 20 and the lower surface 26, is selectively adjustable by rotation of the adjustment member 32.

A beam 100 extends between the upper arm 14 and the lower arm 16 providing stiffness through the upper arm 14 and lower arm 16. A slit 102 extends through the beam 100 between the upper arm 14 and the lower arm 16 permitting movement of the upper arm 14 when the adjustment member 32 is rotated. The alternative embodiment 98 may include the structure described above where the beam 100 does not prevent such structure from being incorporated into the alternative embodiment 98. The base section 18 may be formed by a back edge of the beam 100 or may extend a full length across the upper arm 14 and lower arm 16.

A channel 104 may be provided extending through the beam 100. The opening 62 is aligned with the channel 104. The adjustment shaft 64 extends from the adjustment member 32 through the channel 104 and into the opening 62 through the base section 18.

The slit 102 divides the beam 100 into an upper section 106 extending from the upper arm 14 and a lower section 108 extending from the lower arm 16. The slit 102 may define a tongue 110 and groove 112 positioned in and extending along a length of the beam 100 between the upper section 106 of the beam 100 and the lower section 108 of the beam 100. The tongue 110 is positioned in the groove 112 providing structural support laterally preventing twisting of the upper arm 14 relative to the lower arm 16.

The adjustment member 32 may be is seated in an upper slot 114 in the upper extension 54 and a lower slot 116 in the lower extension 56. The upper slot 114 may also be provided in the embodiment of the device 10 as shown in FIGS. 1 through 6. The upper slot 114 and lower slot 116 may also be integrated directly into the upper arm 14 and the lower arm 16 respectively.

Figure 5:
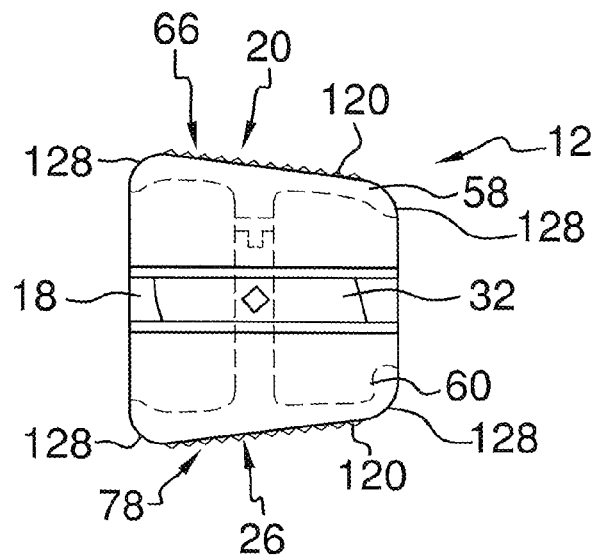
FIG. 5 is a front view of an embodiment of the disclosure for use in a TLIF surgical approach.
Figure 6:
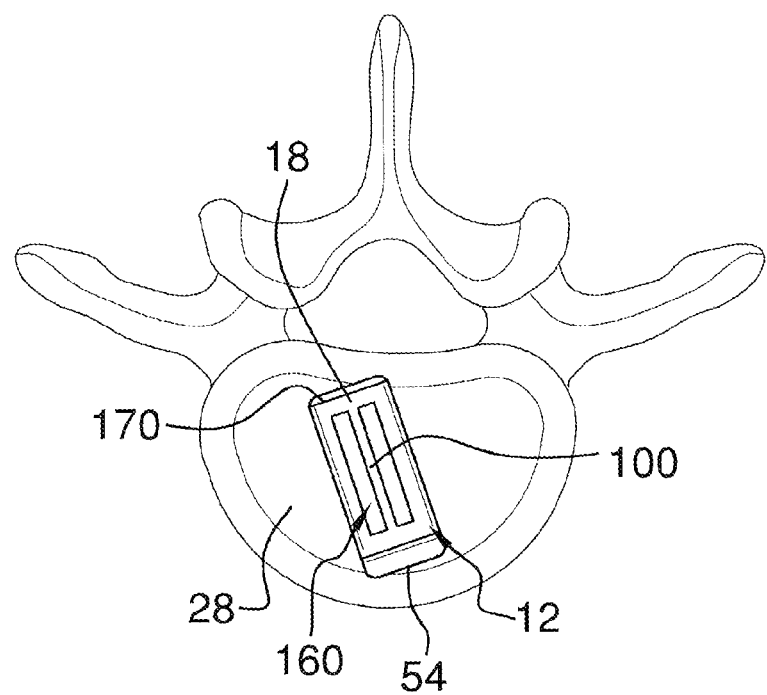
FIG. 6 is a top view of an embodiment of the disclosure using a TLIF surgical approach.
Figure 7:
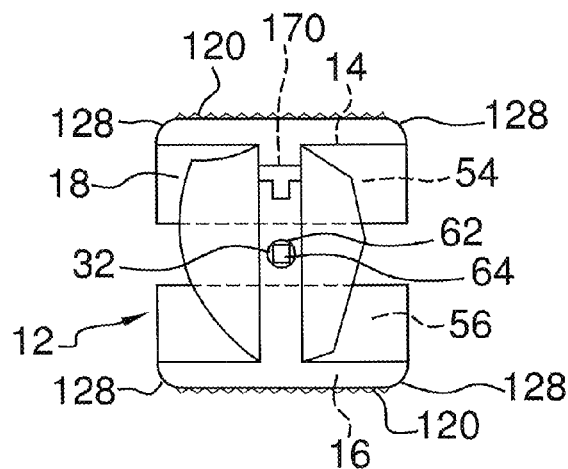
FIG. 7 is a back view of an embodiment of the disclosure for use in a PLIF surgical approach.

The frame 12 may typically be inserted from posterior approach with a technique known as a posterior lumbar interbody fusion (PLIF) or the frame 12, described below and exemplified in FIG. 5, may be used with inserting the frame 12 obliquely from the posterior approach with the technique known as a transforaminal lumbar interbody fusion (TLIF). With both, the goal is still to adjust front to back curvature of the spine 30 (or sagittal plane). Thus, in the TLIF approach the frame 12 is inserted obliquely between the adjacent vertebral bodies 28 and the upper surface 20 and lower surface 26 are angled such that they remain in the proper front to back orientation to provide desired lordosis when the frame 12 is positioned between the adjacent vertebral bodies 28. This is similar to the embodiment in FIG. 5 wherein the upper surface 20 of the upper arm 14 and the lower surface 26 of the lower arm 16 may also be angled relative to each other to further provide for lateral spacing of the discs 28 to adjust lateral curvature of the spine 30 as well as front to back lordosis. The relative planes of the upper surface 20 of the upper arm 14 and the lower surface 26 of the lower arm 16 are determined based on the desired end position after the adjustment member 32 has been moved.

As can be seen generally in FIGS. 5, 7, 13, and 14, a plurality of serrations 120 is positioned on and may be coextensive with the upper surface 20 of the upper arm 14. An upper surface of the beam 100 may be coplanar with the upper surface 20 of the upper arm 14 and also have serrations 120. Similarly, the lower surface 26 of the lower arm 16 also has serrations 120 to prevent slippage and provide secure engagement of the device 10 to each vertebral body 28. A bottom surface of the beam 100 is similarly coplanar with the lower surface 26 and includes serrations 120. Edges 128 may be curved to extend smoothly away from the upper surface 20 and lower surface 26. The edges 128 are smooth without serration to facilitate insertion and positioning of the frame 12 with minimal trauma to the patient.

The outer perimeter edge 34 of the adjustment member 32 may have a plurality of opposed substantially parallel straight sections 38. Each of the opposed straight sections 38 is a unique distance apart with respect to each other opposed straight sections 38 on the adjustment member 32. Alternatively, the outer perimeter edge 34 of the adjustment member 32 may have a curved section 40 and a plurality of straight sides 42. Each straight side 42 is positioned opposite the curved section 40. Each straight side 42 is a unique distance measured transversely from the straight side 42 to the curved section 40 with respect to each other straight side 42. The curved section 40 facilitates smooth rotation of the adjustment member 32 to minimize potential trauma to the surrounding tissues while the adjustment member 32 is rotated. A junction 44 between each of the straight sections 38 may be curved wherein the junctions 44 are configured for facilitating smooth rotation of the adjustment member 32 between the upper arm 14 and the lower arm 16 while still permitting each straight section 38 to rest against the upper arm 14 or lower arm 16 to facilitate retaining the adjustment member 32 in the desired final position. Similarly, a junction 46 between each of the straight sides 42 may be arcuate wherein the junctions 46 are configured for facilitating smooth rotation of the adjustment member 32 between the upper arm 14 and the lower arm 16 while allowing the straight sides 42 to hold the adjustment member in the desired final position.

To enhance support the upper arm 14 and lower arm 16 the adjustment member 32 may be positioned proximate a distal end 48 of the upper arm 14 and a distal end 50 of the lower arm 16 relative to the base section 18 of the frame 12. An upper extension 54 is coupled to and extends from the distal end 48 of the upper arm 14 relative to the base section 18 and a lower extension 56 is coupled to and extends from the distal end 50 of the lower arm 16 relative to the base section 18. The upper extension 54 and the lower extension 56 extend towards each other while extending away from the base section 18 of the frame 12 to facilitate insertion into a patient and positioning between the vertebral bodies 28. Outwardly facing surfaces 58,60 of the upper extension 54 and the lower extension 56 may be curved or otherwise shaped to facilitate insertion and proper positioning with minimal trauma to surrounding tissues.

The adjustment member 32 may be provided in a variety of sizes such that for one adjustment member 32 an angle between the upper surface 20 of the upper arm 14 and the lower surface 26 of the lower arm 16 is selectively adjustable between zero degrees and six degrees in two degree increments. For another adjustment member 32 an angle between the upper surface 20 of the upper arm 14 and the lower surface 26 of the lower arm 16 may be selectively adjustable between six degrees and twelve degrees in two degree increments. Another adjustment member 32 may be provided such that an angle between the upper surface 20 of the upper arm 14 and the lower surface 26 of the lower arm 16 is selectively adjustable between eight degrees and fourteen degrees in two degree increments. Yet another adjustment member 32 may be provided such that an angle between the upper surface 20 of the upper arm 14 and the lower surface 26 of the lower arm 16 is selectively adjustable between ten degrees and nineteen degrees in three degree increments. Still another adjustment member 32 may be provided such that an angle between the upper surface 20 of the upper arm 14 and the lower surface 26 of the lower arm 16 is selectively adjustable between ten degrees and sixteen degrees in two degree increments. Still yet another adjustment member 32 may be provided such that an angle between the upper surface 20 of the upper arm 14 and the lower surface 26 of the lower arm 16 is selectively adjustable between twelve degrees and twenty one degrees in three degree increments. Other ranges and incremental changes may be provided as desired.

In use, the device 10 provides dynamic movement of the upper arm 14 and lower arm 16 allowing for a method 70 of spinal adjustment to correct sagittal balance by dynamic movement or adjustment of the device 10 while the device 10 is in place engaging adjacent vertebral bodies 28. The method 70 comprises a step 72 of having one or more frames 12 each having an associated adjustment member 32 as described above. The method 70 includes another step 74 of inserting each frame 12 between an associated adjacent pair of vertebral endplates 92,94 wherein an upper surface 66 of the frame 12, which may be the upper surface 20 of the upper arm 14, abuts an upper one of the vertebral endplates 92 and a lower surface 78 of the frame 12, which may be the lower surface 26 of the lower arm 16, abuts a lower one of the vertebral endplates 94. This may be done after removing an intervertebral disc. Another step 88 is performed by adjusting an angle between the upper surface 66 and the lower surface 76 of each frame 12 wherein an angle between the associated pair of vertebral endplates 92,94 is adjusted. The method 70 may include adjustment of only one pair of vertebral endplates 92,94 but may also comprise adjusting a cumulative angle between each of multiple pairs of vertebral endplates 92,94 to adjust alignment of the spine 30 formed by a plurality of vertebral bodies 28 relative to pre-determined reference lines determined from measurements of pelvic incidence. Additional factors may include pelvic tilt and C7 plumb line. Desired angles between each pair of vertebral endplates 92,94 may be determined according to the chart of FIG. 12. Additional factors for each particular patient may also be taken into account in addition to pelvic incidence, pelvic tilt and C7 plumb line when determining exact lordosis corrections between specific adjacent vertebral bodies 28.

As shown in FIG. 12, total lumbar lordosis (LL) required is well estimated by the formula LL=pelvic incidence (PI) plus ten (10) degrees, or using a more rigid formula wherein LL=0.56×PI+33. Current practice is for two-thirds of the cumulative lordosis correction to be provided in between the L4/5 and L5/S1 vertebral bodies and the remaining correction divided evenly between L1/2, L2/3, and L3/4 vertebral bodies. These formulas provide a framework for determining the patient's sagittal imbalance that may need correction. Other factors may be included in determining total corrective lordosis if there is a positive sagittal imbalance on standing 36-inch radiographs as determined by the C7 plumb line. For example, a patient with hyper thoracic kyphosis may require additional lumbar lordosis to provide desired results.

Figure 13:
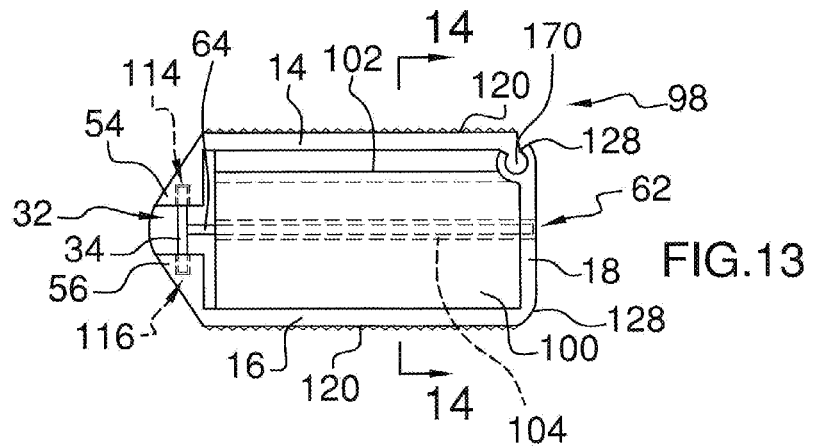
FIG. 13 is a side view of an embodiment of the disclosure.
Figure 14:
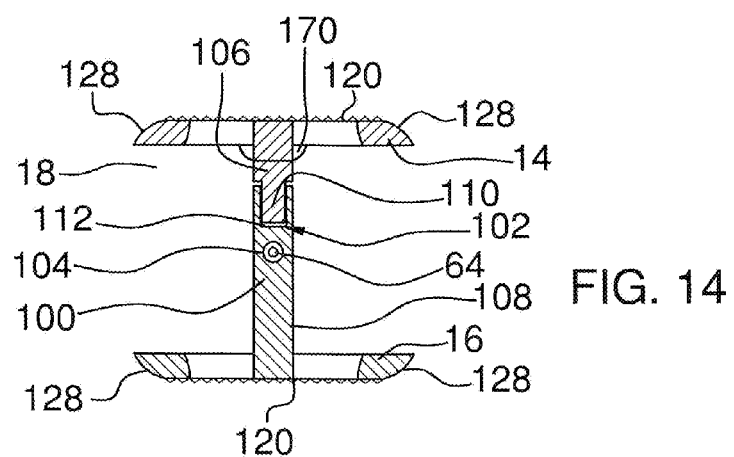
FIG. 14 is a cross-sectional view of an embodiment of the disclosure taken along line 14-14 of FIG. 13.
Figure 15:
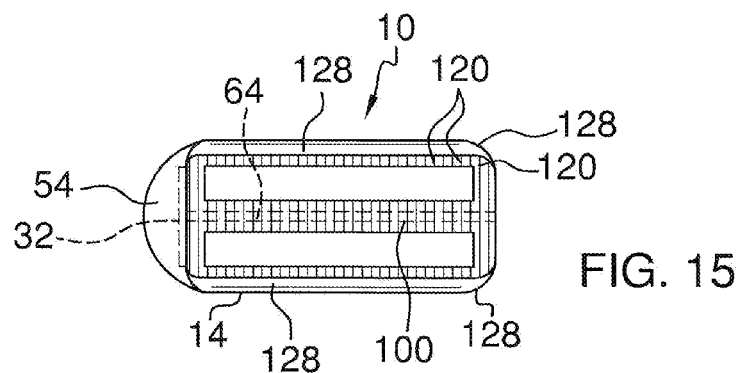
FIG. 15 is a top view of an embodiment of the disclosure.

As demonstrated in FIG. 12, pelvic incidence is measured by drawing a line 130 from the midpoint 132 of the S1 superior endplate 134 to the center of the midpoint 136 between both femoral heads. A second line 138 is drawn parallel to a perpendicular line from the S1 endplate 134 with the starting point at the midpoint 132 of the S1 superior endplate 134. The angle 140 measured between these two lines 130,138 is the pelvic incidence. This measurement defines the relationship between the spine and the pelvis and can be used to predict the amount of lumbar lordosis needed to maintain a neutral sagittal balance. As also shown in FIG. 14, pelvic tilt is measured using the line 130 from the midpoint 136 between the center of the femoral heads to the midpoint 132 of the S1 superior endplate 134. A vertical reference line 142 is drawn vertically from the midpoint 136 between both femoral heads. An angle 144 created between the line 130 and the vertical reference line 142 represents the pelvic tilt. The angle 144 helps the surgeon determine if the patient is compensating for lack of lumbar lordosis by increasing their pelvic tilt to maintain a neutral sagittal balance. As shown in FIG. 13, C7 plumb line 146 is drawn on a 36 inch lateral radiograph by finding the middle of the C7 vertebral body 148 and drawing a vertical line downward. A measurement from the posterior superior corner 150 of the S1 vertebral endplate 134 to the C7 plumb line 146 is measured. This determines the patient's sagittal balance. A positioning of the C7 plumb line 146 posterior to the superior corner 154 of the S1 endplate is considered a negative sagittal balance, and a positive value is noted when the C7 plumb line 146 is anterior to the posterior superior corner 150 of the S1 vertebral endplate 134. A positive sagittal balance value of greater than 5 centimeters is considered abnormal.

Figure 8:
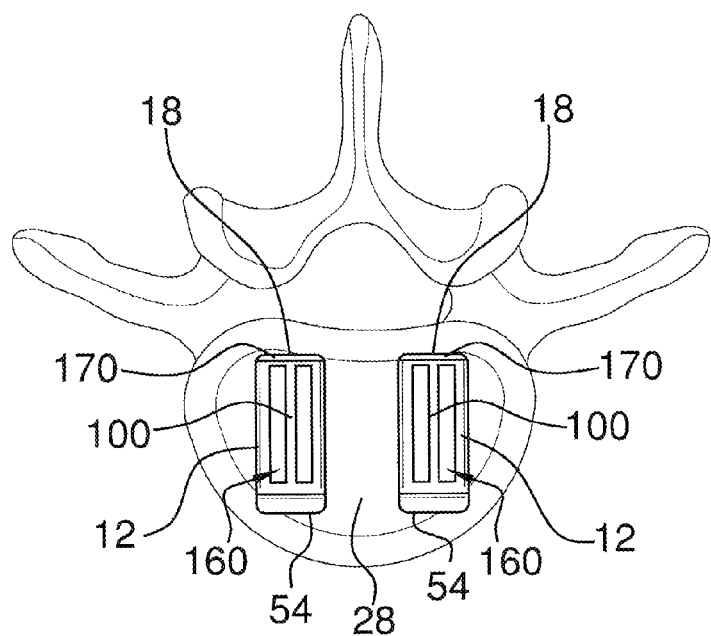
FIG. 8 is a top view of an embodiment of the disclosure using a PLIF surgical approach.
Figure 9:
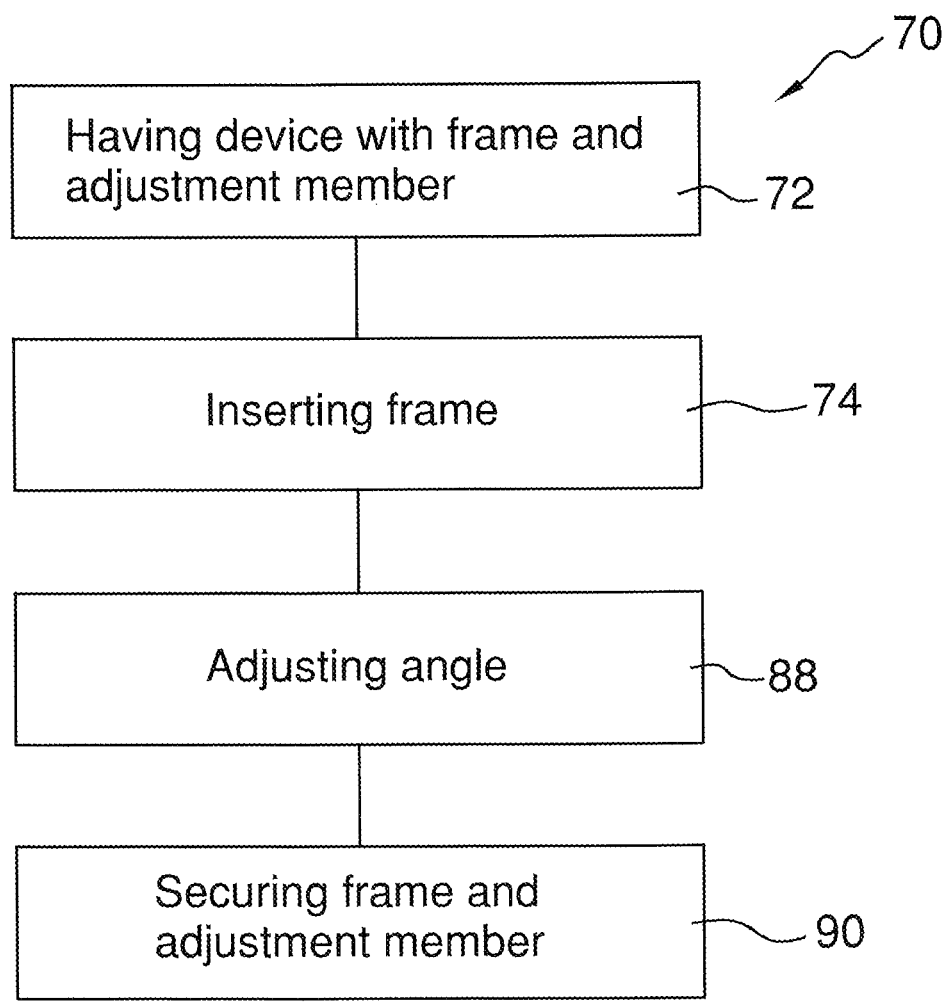
FIG. 9 is a schematic view of a method according to an embodiment of the disclosure.
Figure 10:
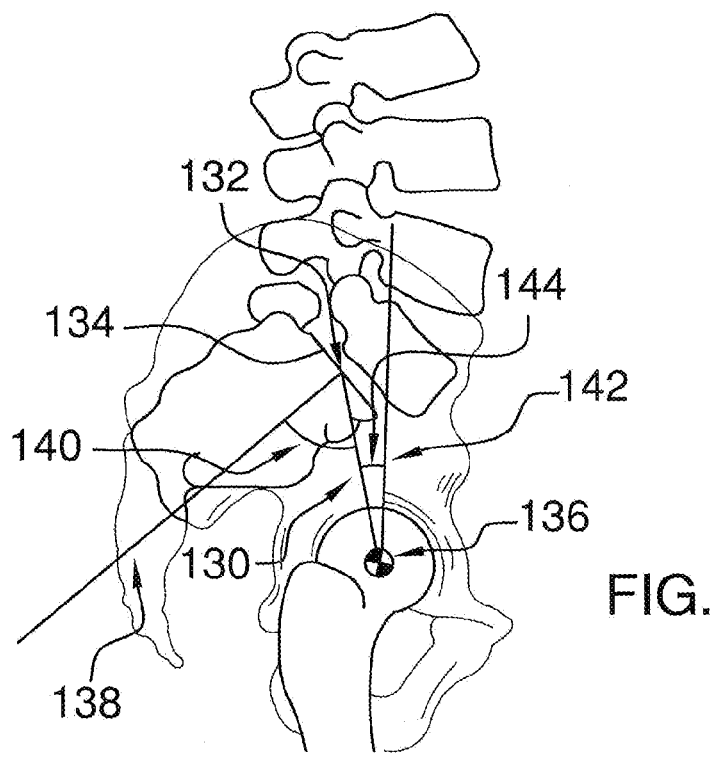
FIG. 10 is a side view demonstrating measurement of pelvic incidence.
Figure 11:
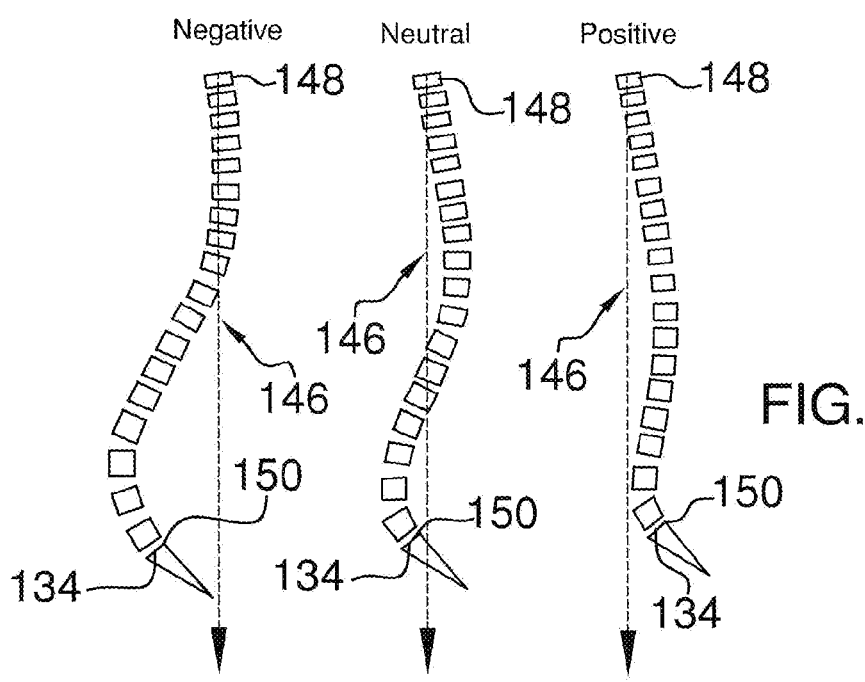
FIG. 11 is a side view demonstrating spinal alignment relative to a C7 plumb line.

With the above information for a particular patient, incremental adjustment between adjacent vertebral endplates 92,94 may be determined consistent with FIG. 8 and any additional factors deemed necessary to provide the desired total cumulative adjustment of the spine 30 relative to the position of the pelvis 82 to reestablish sagittal balance as opposed to merely straightening the spine 30 alone. After the adjustment member 32 is rotated to provide a desired angle between adjacent vertebral bodies 28, another step 90 may be performed wherein pedicle screws are placed to stabilize the spine and maintain the desired position. Pressure on the frame 12 may hold the frame 12 in place while the pedicle screws are placed. The permanent alignment is held by the pedicle screws and rod construct or by other posterior fixation methods.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An inter-vertebral spinal insert cage device comprising:
    an upper arm, said upper arm having a substantially planar upper surface;
    a lower arm, said lower arm having a substantially planar lower surface;
    a hinge coupled between said upper arm and said lower arm wherein said upper arm is pivotable relative to said lower arm to adjust an angle of said planar upper surface relative to said planar lower surface;
    an adjustment member positioned between said upper arm and said lower arm, said adjustment member being manipulatable whereby an angle between said upper arm and said lower arm is selectively adjustable by manipulation of said adjustment member;
    a beam extending between said upper arm and said lower arm, said beam having an upper edge fixedly coupled to said upper arm, said beam having a lower edge fixedly coupled to said lower arm; and
    a slit extending through said beam between said upper arm and said lower arm, said slit dividing said beam into an upper section extending from said upper arm and a lower section extending from said lower arm, said upper section of said beam abutting said lower section of said beam when said upper arm is in an unpivoted position, said slit extending fully through said beam wherein said upper arm is pivotable away from said lower arm such that said angle between said upper arm and said lower arm is selectively adjustable by manipulation of said adjustment member.

2. The device of claim 1, further comprising an outer perimeter edge of said adjustment member having a plurality of opposed straight sections, each of said opposed straight sections being a unique distance apart with respect to each other.

3. The device of claim 1, further comprising an outer perimeter of said adjustment member having a curved section and a plurality of straight sides, each straight side being positioned opposite said curved section, each straight side being a unique distance measured transversely from said straight side to said curved section with respect to each other straight side.

4. The device of claim 1, further comprising said adjustment member being positioned proximate a distal end of said upper arm and a distal end of said lower arm relative to said hinge.

5. The device of claim 1, further comprising:
an upper extension coupled to and extending from a distal end of said upper arm relative to said hinge; and
a lower extension coupled to and extending from a distal end of said lower arm relative to said hinge, said upper extension and said lower extension extending towards each other while extending away from said hinge.

6. The device of claim 1, further comprising:
a channel extending through said beam; and
an adjustment shaft extending from said adjustment member, said adjustment shaft having a distal end relative to said adjustment member extending through said channel, said distal end of said adjustment shaft being configured for being engaged by a tool wherein said adjustment member is rotatable by manipulating the tool.

7. The device of claim 2, further comprising a junction between each of said straight sections being curved wherein said junctions are configured for facilitating smooth rotation of said adjustment member between said upper arm and said lower arm.

8. The device of claim 3, further comprising a junction between each of said straight sides being arcuate wherein said junctions are configured for facilitating smooth rotation of said adjustment member between said upper arm and said lower arm.

9. The device of claim 1, further comprising an angle between said upper surface of said upper arm and said lower surface of said lower arm being selectively adjustable between zero degrees and six degrees in two degree increments.

10. The device of claim 1, further comprising an angle between said upper surface of said upper arm and said lower surface of said lower arm being selectively adjustable between six degrees and twelve degrees in two degree increments.

11. The device of claim 1, further comprising an angle between said upper surface of said upper arm and said lower surface of said lower arm being selectively adjustable between eight degrees and fourteen degrees in two degree increments.

12. The device of claim 1, further comprising an angle between said upper surface of said upper arm and said lower surface of said lower arm being selectively adjustable between ten degrees and nineteen degrees in three degree increments.

13. The device of claim 1, further comprising an angle between said upper surface of said upper arm and said lower surface of said lower arm being selectively adjustable between ten degrees and sixteen degrees in two degree increments.

14. The device of claim 1, further comprising an angle between said upper surface of said upper arm and said lower surface of said lower arm being selectively adjustable between twelve degrees and twenty one degrees in three degree increments.

15. The device of claim 1, further comprising said slit defining a tongue and groove positioned in said beam between said upper section of said beam and said lower section of said beam, said tongue being positioned in said groove.

16. The device of claim 6, further comprising:
said channel extending through said lower section of said beam; and
said slit defining a tongue and groove positioned in said beam between said upper section of said beam and said lower section of said beam, said tongue being positioned in said groove.

17. The device of claim 1, further comprising:
an upper slot coupled to said upper arm;
a lower slot coupled to said lower arm; and
said outer perimeter edge of said adjustment member being seated in said upper slot and said lower slot wherein said adjustment member is inhibited from disengaging said upper arm and said lower arm.

18. The device of claim 1, further comprising a plurality of serrations being positioned on and coextensive with said upper surface of said upper arm and said lower surface of said lower arm.

19. The device of claim 1, further comprising said hinge being positioned adjacent to and between respective proximal ends of said upper arm and said lower arm.

20. An inter-vertebral spinal insert cage device comprising:
an upper arm, said upper arm having a substantially planar upper surface;
a lower arm, said lower arm having a substantially planar lower surface;
a base section coupled to and extending between said upper arm and said lower arm wherein said upper arm, said lower arm and said base section define a frame, each of said upper arm and said lower arm extending outwardly from said base section;
a hinge coupling one of said upper arm and said lower arm to said base section wherein said one of said upper arm and said lower arm is pivotable relative to said base section such that said planar upper surface is pivoted about a single pivot point adjusting an angle of said planar upper surface relative to said planar lower surface; and
an adjustment member positioned between said upper arm and said lower arm, said adjustment member being manipulatable whereby an angle between said upper arm and said lower arm is adjusted such that said planar upper surface is pivoted relative to said planar lower surface by manipulation of said adjustment member.

21. The device of claim 20, further comprising an outer perimeter edge of said adjustment member having a plurality of opposed straight sections, each of said opposed straight sections being a unique distance apart with respect to each other.

22. The device of claim 20, further comprising an outer perimeter of said adjustment member having a curved section and a plurality of straight sides, each straight side being positioned opposite said curved section, each straight side being a unique distance measured transversely from said straight side to said curved section.

23. The device of claim 20, further comprising said adjustment member being positioned proximate a distal end of said upper arm and a distal end of said lower arm relative to said base section of said frame.

24. The device of claim 20, further comprising:
an upper extension coupled to and extending from a distal end of said upper arm relative to said base section; and
a lower extension coupled to and extending from a distal end of said lower arm relative to said base section, said upper extension and said lower extension extending towards each other while extending away from said base section of said frame.

25. The device of claim 21, further comprising a junction between each of said straight sections being curved wherein said junctions are configured for facilitating smooth rotation of said adjustment member between said upper arm and said lower arm.

26. The device of claim 22, further comprising a junction between each of said straight sides being arcuate wherein said junctions are configured for facilitating smooth rotation of said adjustment member between said upper arm and said lower arm.

27. The device of claim 20, further comprising said angle of said upper surface of said upper arm relative to said lower surface of said lower arm being selectively adjustable between zero degrees and six degrees in two degree increments.

28. The device of claim 20, further comprising said angle of said upper surface of said upper arm relative to said lower surface of said lower arm being selectively adjustable between six degrees and twelve degrees in two degree increments.

29. The device of claim 20, further comprising said angle of said upper surface of said upper arm relative to said lower surface of said lower arm being selectively adjustable between eight degrees and fourteen degrees in two degree increments.

30. The device of claim 20, further comprising said angle of said upper surface of said upper arm relative to said lower surface of said lower arm being selectively adjustable between ten degrees and nineteen degrees in three degree increments.

31. The device of claim 20, further comprising said angle of said upper surface of said upper arm relative to said lower surface of said lower arm being selectively adjustable between ten degrees and sixteen degrees in two degree increments.

32. The device of claim 20, further comprising said angle of said upper surface of said upper arm relative to said lower surface of said lower arm being selectively adjustable between twelve degrees and twenty one degrees in three degree increments.

* * * * *